United States Patent [19]

Taheri

[11] Patent Number: 4,851,001
[45] Date of Patent: Jul. 25, 1989

[54] PROSTHETIC VALVE FOR A BLOOD VEIN AND AN ASSOCIATED METHOD OF IMPLANTATION OF THE VALVE

[76] Inventor: Syde A. Taheri, 268 Dan Troy, Williamsville, N.Y. 14221

[21] Appl. No.: 141,553

[22] Filed: Jan. 7, 1988

Related U.S. Application Data

[63] Continuation-in-part of Ser. No. 99,302, Sep. 17, 1987, abandoned.

[51] Int. Cl.$^4$ .............................................. A61F 6/24
[52] U.S. Cl. ............................................ 623/2; 623/1
[58] Field of Search ..................... 623/1, 2, 66, 11, 12

[56] References Cited

U.S. PATENT DOCUMENTS

| | | |
|---|---|---|
| 15,192 | 6/1856 | Peale . |
| 2,877,792 | 3/1959 | Tybus ..................................... 623/2 |
| 3,312,237 | 4/1967 | Mon ........................................ 623/2 |
| 3,683,926 | 8/1972 | Sazuki . |
| 3,717,883 | 2/1973 | Mosher . |
| 4,086,665 | 5/1978 | Poirier . |
| 4,118,806 | 10/1978 | Porier . |
| 4,159,543 | 7/1979 | Carpentier . |
| 4,190,909 | 3/1980 | Ablaza ..................................... 623/1 |
| 4,254,508 | 3/1981 | Bokros . |
| 4,259,753 | 4/1981 | Liotta ...................................... 623/2 |
| 4,350,492 | 9/1982 | Wright . |
| 4,406,022 | 9/1983 | Roy . |
| 4,605,408 | 8/1986 | Carpentier ............................. 623/2 |

Primary Examiner—Richard J. Apley
Assistant Examiner—James Prizant
Attorney, Agent, or Firm—Sommer & Sommer

[57] ABSTRACT

A prosthetic valve and an associated method of implanting the valve within a blood vein utilize a valve support ring and a pair of leaflet members pivotally connected to the ring. The valve is positionable within a radial plane of the blood vessel for permitting substantially unidirectional flow through the blood vein. The support ring is not required to be sutured within a blood vein and instead includes an outer surface defining a radially outwardly-directed annular groove, so that the valve can be secured within the blood vein by means of a cord tied around of the blood vein and in a tightened condition within the annular groove. The support ring is held in such fixed position along the length of the blood vein because the blood vein is held between the support ring outer surface and the cord. Furthermore, the support ring outer surface is contoured in such a manner so that when the valve is operatively secured within a blood vein, the inner wall of the blood vein lies in substantial conformity to the shape of the ring outer surface.

17 Claims, 3 Drawing Sheets

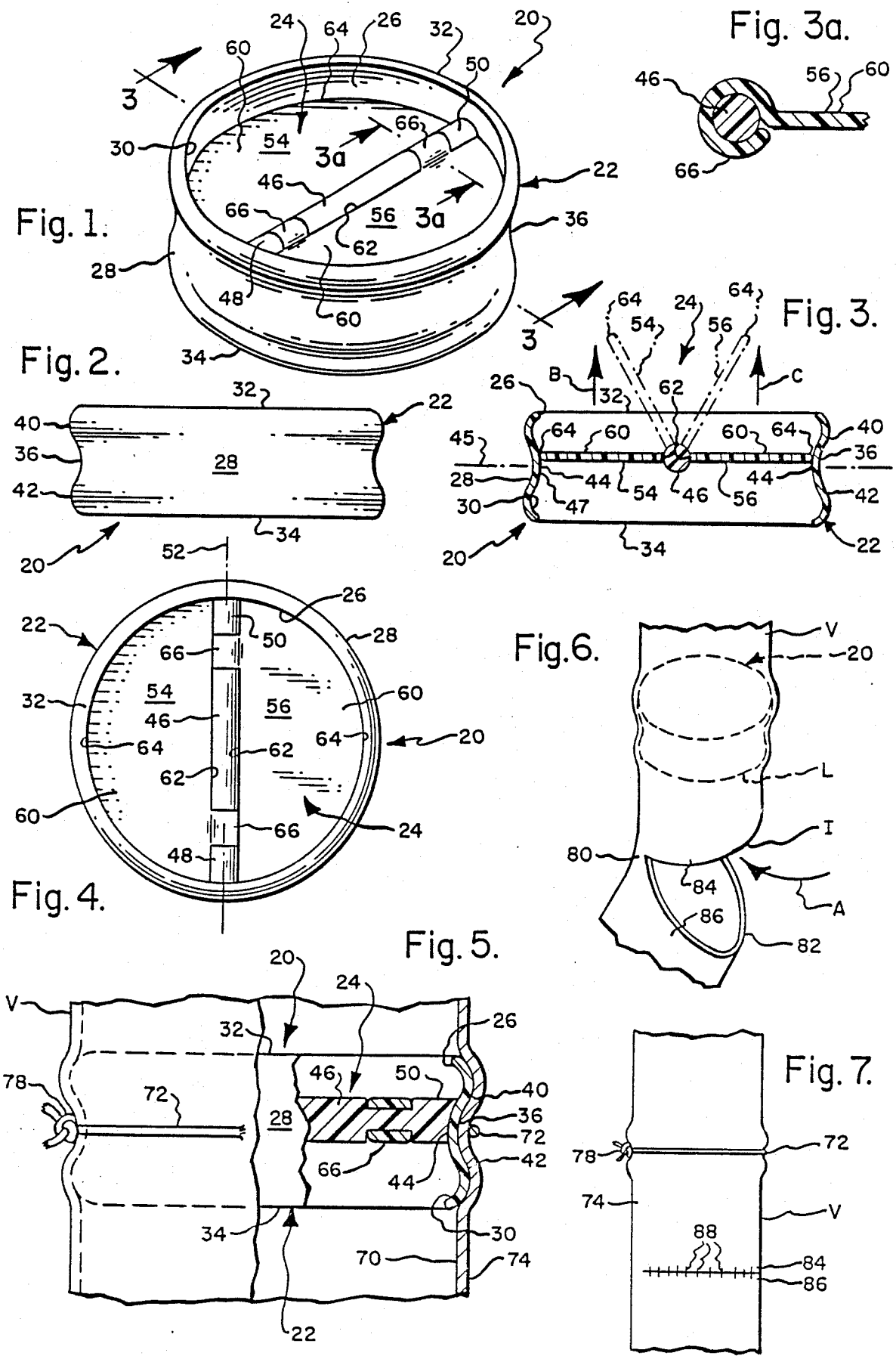

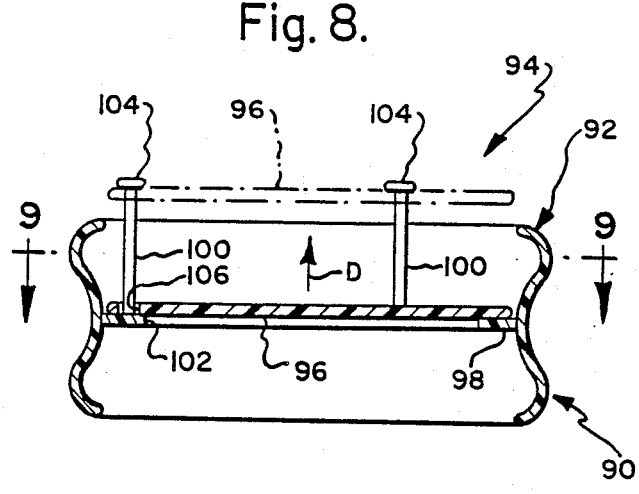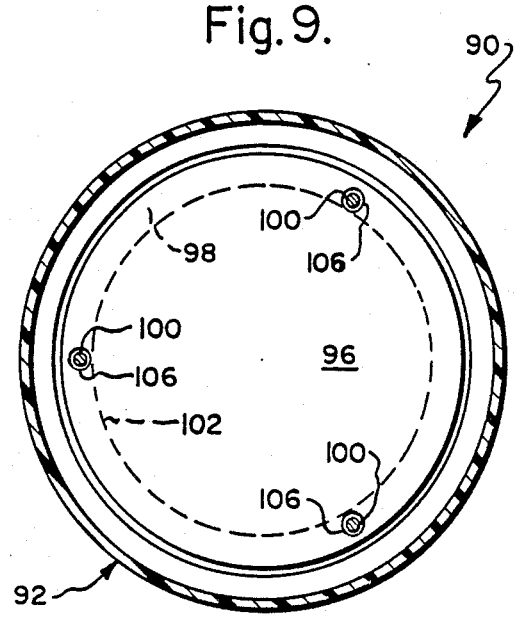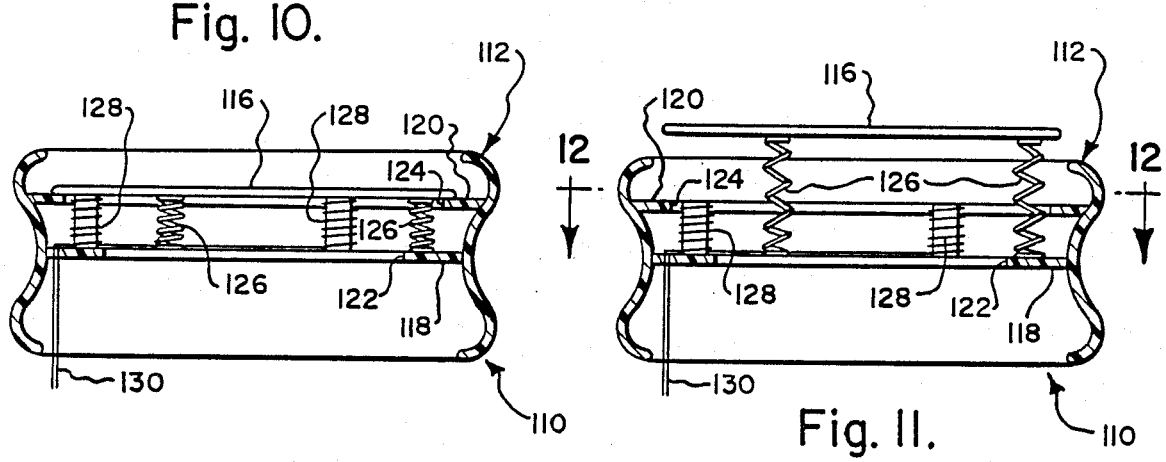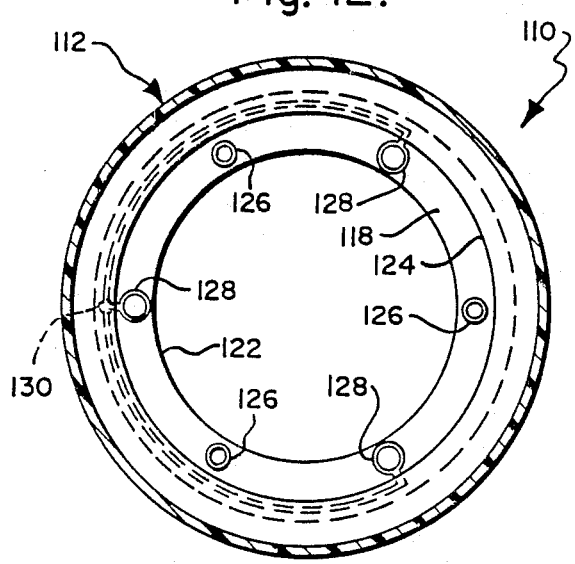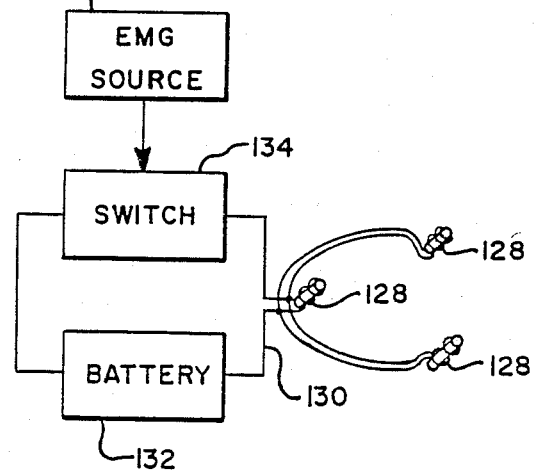

4,851,001

PROSTHETIC VALVE FOR A BLOOD VEIN AND AN ASSOCIATED METHOD OF IMPLANTATION OF THE VALVE

BACKGROUND OF THE INVENTION

This is a continuation-in-part application of my co-pending patent application Ser. No. 099,302, filed Sept. 17, 1987 (abandoned).

This invention relates generally to valves for use in a living body and relates more particularly to a prosthetic valve for use in a blood vein.

The type of valve with which this invention is concerned includes an annular support member or ring defining an opening therethrough, and leaflets hingedly attached to the support ring for opening and closing the support ring opening in a manner permitting substantially unidirectional flow therethrough. An example of such a valve is shown and described in U.S. Pat. No. 3,717,883.

Characteristically, prior art valves such as the one described in the referenced patent are designed to be sutured or sewn into place within a blood vessel. To this end, the support ring of the valve is secured within a flexible fabric tube at a location generally medially of the tube. The blood vessel then is completely severed in two to provide two free ends, and each end of the fabric tube, within which the valve is secured, is sutured or sewn to a corresponding one of the free blood vessel ends to effectively splice the blood vessel. Such an implantation process is known to be relatively time-consuming.

A limitation associated with comparable prior art valves relates to the likelihood of clotting of blood about the support member of the valve. Such clotting is, of course, undesirable and is believed to be promoted by the fabric tube commonly utilized when suturing the valve into place. In particular, the fabric of the tube normally defines regions or voids within which blood is permitted to accumulate and clot. Furthermore, the fabric of the tube commonly defines with the support ring, gaps or spaces between the outer surface of the support ring and the inner wall of the fabric tube, which permit the buildup of blood therein. It is known that the surface of the support rings of such prior art valves can be coated with an inert substance, such as pyrolite carbon, in order to reduce the buildup of blood thereupon and hence reduce the likelihood of blood clotting about the support ring surface, but the cost required to coat the support ring with such a substance is relatively high.

It is, accordingly, an object of the present invention to provide a new and improved valve for a blood vein which is not required to be sutured into place, and a method of implanting the valve within a vein, which does not require a complete severance of the vein for implantation purposes.

Another object of the present invention is to provide such a valve including a support ring which reduces the likelihood of blood clotting thereabout.

Still another object of the present invention is to provide such a valve having a support ring which may not require a coating of an inert substance in order to reduce the likelihood of such clotting.

Yet still another object of the present invention is to provide such a valve having a support ring to which the tissue of a blood vein effectively seats.

A further object of the present invention is to provide such a valve which is economical to construct and effective in operation.

SUMMARY OF THE INVENTION

This invention resides in a prosthetic valve for a blood vein and an associated method of implanting the valve within the vein.

The valve of this invention includes means defining a support ring positionable within a blood vein and leaflet means connected to the support ring in a manner permitting substantially unidirectional flow through the ring. The support ring has an outer surface in which is defined a radially outwardly-opening annular groove so that when the support ring is positioned within the blood vein and oriented generally within a radial plane thereof, the support ring can be secured therein by means of a cord tied around the blood vein and in a tightened condition within the annular groove so that the support ring is held in position along the length of the blood vein as the blood vein is held between the support ring outer surface and the cord.

The method of implanting the valve within a blood vein includes a step of forming an opening in the blood vein at a location therealong which is spaced from the blood vein location at which the valve is desired to be implanted. The step of forming an opening preferably includes a step of cutting the blood vein for a substantial distance around, but not all of, the circumference of the vein so that the vein is not severed in two. The prosthetic valve is then inserted through the formed opening to the location within the blood vein at which the valve is desired to be implanted and oriented so that its support ring is oriented generally in a radial plane of the blood vein. Cord means is then provided and tied about the outer wall of the blood vein and in a tightened condition within the annular grooves so that the support ring is held in position along the length of the blood vein as the blood vein is held between the support ring outer surface and the cord. Hence, the valve is not sutured into place within a blood vein.

BRIEF DESCRIPTION OF THE DRAWING FIGURES

FIG. 1 is a perspective view of an embodiment of a prosthetic valve in accordance with the present invention.

FIG. 2 is an elevational view of the FIG. 1 valve, as seen generally from one side in FIG. 1.

FIG. 3 is a cross-sectional view taken generally on line 3—3 of FIG. 1.

FIG. 3a is a fragmentary cross-sectional view taken generally on line 3a—3a of FIG. 1.

FIG. 4 is a plan view of the FIG. 1 valve, as seen from above in FIG. 2.

FIG. 5 is a fragmentary plan view, shown partially in section, of a blood vein within which the FIG. 1 valve is operatively positioned.

FIG. 6 is a fragmentary perspective view of a blood vein having an incision formed therein and through which the FIG. 1 valve is inserted when the valve is operatively positioned within the blood vein.

FIG. 7 is a fragmentary plan view of the FIG. 6 blood vein at the completion of the valve implantation process in accordance with the present invention.

FIG. 8 is a view similar to that of FIG. 3 of an alternative embodiment of the valve in accordance with the present invention.

FIG. 9 is a cross-sectional view taken generally on line 9—9 of FIG. 8.

FIG. 10 is a view similar to that of FIG. 3 of another embodiment of the valve in accordance with the present invention illustrating the valve in a closed condition.

FIG. 11 is a view similar to that of FIG. 10, illustrating the FIG. 10 valve in an open condition.

FIG. 12 is a cross-sectional view taken generally on line 12—12 of FIG. 11.

FIG. 13 is a view showing in block diagram form the control circuit for the valve of FIGS. 10-12.

DETAILED DESCRIPTION OF THE ILLUSTRATED EMBODIMENTS

Figure 14:
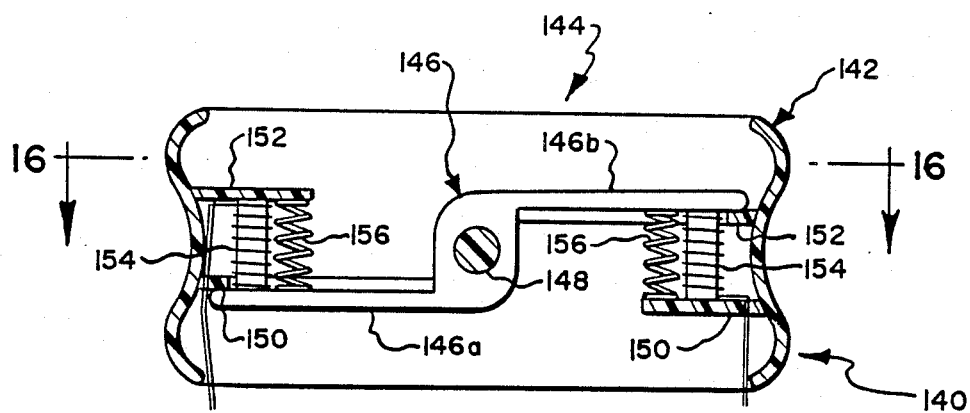
FIG. 14 is a view similar to that of FIG. 10 of still another embodiment of the valve in accordance with the present invention illustrating the valve when in a closed condition.

Turning now to the drawings in greater detail and considering first FIG. 1, there is shown an embodiment, generally indicated 20 of a prosthetic valve in accordance with the present invention for implantation within a blood vein V (FIGS. 5 and 6). The valve 20 includes means defining a support ring 22 and leaflet means, generally indicated 24, connected to the support ring 22 for movement relative thereto. As will be explained in greater detail hereinafter, the support ring 20 defines a generally circular-shaped opening 26, and the leaflet means 24 cooperate with the support ring 22 to permit substantially one-directional or unidirectional flow through the support ring opening 26. Therefore, when the valve 20 is operatively positioned within a blood vein, the valve 20 permits flow of blood through the vein in only one direction.

With reference to FIGS. 1-4, the support ring 22 is ring-like in shape and defines an outer surface 28, an inner surface 30 and two opposite end surfaces 32,34 extending between the outer and inner surfaces 28 and 30. In accordance with the present invention, the outer surface 28 of the ring 22 defines an annular groove therearound, which groove 36 faces generally radially outwardly of the ring 22. As will be described herein, the groove 36 facilitates the securement of the valve 20 within the blood vein.

As best shown in FIG. 3, the outer surface 23 is contoured so as to define gentle undulations or waves as a path is traced therealong from one ring end surface 32 to the other ring surface 34. Such undulations provide the groove 36 with relatively smoothly-contoured blunt edges 40,42 on opposite sides thereof. More specifically, each of the groove edges 40 or 42 is rounded in shape, as viewed in the cross-sectional view of FIG. 3, and is devoid of sharp corners.

With reference still to FIG. 3, the inner surface 30 of the ring 22 is contoured so as to be shaped generally complementarily to that of the outer surface 28 so that gentle undulations are defined in the inner surface 30 as the path is traced from one end ring surface 32 to the other ring surface 34. The shape of each inner and outer surface 28 and 30 is symmetrical about transverse a radial midplane, indicated at 45, of the ring 22. Furthermore, there is defined within the inner surface 30, a radially inwardly-directed annular bulge or projection 44 located generally midway between the ring end surfaces 32 and 34 so that its innermost projecting portion, indicated at 47, is contained generally within the ring midplane 45. The support ring 22 can be constructed of any of a number of suitable materials, such as steel, platinum or titanium.

Furthermore, the ring outer surface 28 is preferably roughened or aspirated so as to feel relatively harsh to the touch. Inasmuch as the outer surface 28 is adapted to engage the inner wall of the blood vein in the manner explained hereinafter, the roughness of the outer surface 28 promotes a seating or clinging of the blood vein to the outer surface 28 so that the blood vein and outer surface 28 effectively adhere to or frictionally grip one another when positioned in operative engagement. An effective adherence reduces the likelihood that regions of the blood vein will become detached from the outer surface 28 in a manner creating pockets or voids within which blood is susceptible of accumulating or clotting. Inasmuch as conventional valves are presently coated with an inert substance, such as pyrolite carbon, by means of a relatively costly process to enhance the seat between the blood vein and the support ring of the valve, the outer ring 22 is advantageous in that its roughened surface 28 may circumvent any need that the valve undergo a costly coating process to enhance the seating between the ring outer surface 28 and the blood vein.

With reference to FIGS. 1, 3, and 4, the valve 20 includes a shaft 46 joining the leaflet means 24 to the support ring 22. The shaft 46 is cylindrical in form and defines two opposite ends 48,50. Furthermore, the shaft 46 is arranged within the support ring opening 26 so as to extend generally centrally thereacross and thereby bisect the opening 26. The shaft 46 is press-fit between two locations on the bulge 44 of the inner surface 30, which locations are generally diametrically opposed to one another so that the shaft 46 is fixedly secured to the support ring 22. As best shown in FIGS. 3 and 4 the longitudinal axis, indicated, 52, of the shaft 46 is oriented slightly offset to the radial midplane 45 of the ring 22 so as to be positioned slightly closer to the ring end surface 32 than the ring end surface 34.

The leaflet means 24 includes a pair of flapper-like members 54,56 hingedly joined to the shaft 46 for movement between an open condition, as shown in phantom in FIG. 3, to a closed condition, as shown in solid in FIG. 3. As best shown in FIG. 4, each of the flapper-like members 54,56 is platen-like in shape having a half-moon portion 60 having a straight edge 62 and an arcuate edge 66 and a hinge portion 66 joined along the straight edge portion 64. As best shown in FIG. 3a, each hinge portion 64 is sleeve-like in shape and of such size as to be loosely received about the shaft 46. Along these lines, the inner diameter of the sleeve formed by each hinge portion 66 is slightly larger than diameter of the shaft 46. Both flapper-like members 54 and 56 are constructed of a suitable material, such as steel, platinum or titanium.

With reference again to FIG. 3, the flapper-like members 54,56 are sized so that each spans one-half of the support ring opening 26 and is prevented from pivoting about the shaft from the FIG. 3 solid-line condition toward the ring end surface 34. To this end, the collective diameter of the flapper-like members 54,56 as viewed in the plan view of FIG. 4 is slightly larger than the diameter of the support ring opening 26, as measured across the radial midplane 45, and the flapper-like members 54 and 56 are connected to the shaft 46 so as to be arranged to one side of the ring midplane 45 closer to the ring end surface 32.

Pivotal connection between the flapper-like members 54,56 and the shaft 46 is effected as the hinge portion 66 of each member 54 or 56 is positioned about so as to accept the shaft 46. Therefore, the flapper-like members 54,56 are permitted to pivot relative to the support ring 22 between the FIG. 3 solid-line condition, at which each arcuate edge 64 of the members 54,56 rest in engagement with the surface of the bulge, 44 and the FIG. 3 opened condition at which the plane of arcuate edge 64 is arranged angularly with respect to the radial midplane 45 of the ring 22.

When the flapper-like members 54 and 56 are positioned in the FIG. 3 open or phantom-like condition, the support ring opening 26 is opened so as to permit substantially unrestricted flow of a fluid in the direction of the parallel arrows B and C. Conversely, when the flapper-like members 54,56 are positioned in the FIG. 3 closed or solid-line condition, the opening 26 of the support ring 22 is shut off so as to prevent flow of fluid therethrough in the direction opposite the arrows B and C. It follows from the foregoing that the members 54,56 cooperate with the support ring 22 effectively render the valve 22 to as a check valve permitting flow through the opening 56 only in the direction of the arrows B and C.

With reference to FIG. 5, the valve 20 is positionable within a blood vein V so that its support ring 22 is oriented generally within a radial plane of the blood vein V and so that the inner wall, indicated at 70, of the blood vein closely surrounds the ring outer surface 28. In such a position, the valve 20 is securable by means of a cord 72 tied about the outer wall, indicated at 74 of the blood vein V and tightened within the groove 36. Opposite ends of the cord 72 are tied in a knot 78. The cord 72 is constructed of a suitable material, such as silk, and is of sufficient length to encompass the support ring 22 when tied thereabout.

With the valve operatively positioned and secured within the blood vein V by means of the cord 72, the inner wall 70 of the blood vein V lies in substantial conformity with the shape of the outer surface 28 of the support ring 22. To this end, the minimum diameter of the support ring outer surface 28 is at least as great as the diameter of the vein inner wall 70 so that the engagement between the inner wall 70 and the ring outer surface 28 is continuous from one end surface 32 of the support ring 22 to the other ring end surface 34. Such conformity and engagement of the inner wall 70 with the ring outer surface 28 reduces the likelihood that voids or regions will develop between the inner wall 70 and the ring outer surface 28 within which blood is likely to accumulate and clot. More specifically, the blood vein inner wall 70 is conformed to the gentle undulations in the ring outer surface 28 and is thereby not required to define a sharp corner as a path is traced from one ring end surface 32 to the other ring end surface 34. Furthermore and related to the fact that the ring outer surface 28 is devoid of sharp corners, the wall of the blood vein V is not appreciably deformed about the outer surface 28 when the cord 72 is tightened about the blood vein V.

In order to implant the valve 20 within the blood vein V, an opening 82 is formed in the blood vessel to permit the insertion of the valve 20 within. Such an opening 82 can be formed by incising or making an appropriately-sized incision I across the blood vein V by means of a knife (not shown) or similar cutting tool. The incision I is oriented within a radial plane of the blood vein V and extends for a substantial distance around, but not all of the circumference of the blood vein. Thus, the blood vein V remains joined at the incision I by means of an uncut portion 80. Furthermore and in accordance with the present invention, the incision I is spaced longitudinally from the radial plane or location, indicated at L, at which the valve 20 is desired to be secured.

Once the opening 82 is formed, the valve 20 is inserted therethrough in the direction of the arrow A and directed along the length of the blood vein V until the location L is reached. At that point, the valve 20 is manipulated so that its support ring 22 is arranged within a radial plane of the blood vein V. During insertion of the valve 20 within the blood vein V, care should be taken to ensure that the ring end surface 32 is oriented on the downstream-side of the blood vein location L so that the valve 20 permits blood flow through the blood vein in the direction in which blood flow is desired.

To secure the valve 20 within the blood vein, the cord 72 is provided and then tied around the outer wall of the blood vein and support ring 22 so that the inner wall 70 of the blood vein V conforms substantially to the ring outer surface 28. To this end, the cord 72 is wrapped around the blood vein V and tightened within the annular groove 36 and tied in a knot 78. The valve 20 is thereby prevented from shifting or moving relative to and along the length of the blood vein V as the blood vein walls are secured between the cord 72 and the ring outer surface 36.

Upon securing the valve 20 within the blood vein V by means of the cord 72, the opening 82 is closed. To this end, and with reference to FIG. 7, the opposite sides, indicated at 84 and 86, of the incision I are positioned adjacent one another and stitched together by means of stitches 88.

Inasmuch as conventional valves are commonly sutured in place within a blood vessel in a manner requiring a complete severance of the blood vessels, it is believed that the method of this invention is advantageous in that a complete severance of the vein V for implantation of the valve 20 is not required. The complete blood vessel severance and subsequent splicing involved in conventional suturing processes is believed to contribute to a relatively high possibility of blood clotting in the vicinity of the severed blood vessel ends. Because, on the other hand, the blood vein V is not completely severed by the method of this invention nor does the closing of the opening 82 require stitches completely around the circumference of the vein V, the method of the invention is believed to reduce the likelihood of blood clotting in the vicinity of the opening 82, when closed.

It will be understood from the foregoing that the invention accomplishes its intended objects in that the valve 20 of the invention is adapted to be tied in place within a blood vein by means of a cord 72 tied therearound and its support ring 22 defines an outer surface 38 possessing such contours that a blood vein V tied therearound lies in substantial conformity to the gentle undulations of the ring outer surface 38. Hence, the valve 20 need not be sutured in place within a blood vein, and the need for any fabric tube commonly utilized when suturing the valve in place and which is believed to promote the clotting of blood thereabout is obviated. Furthermore, the method of the invention sets forth the steps involved in operatively implanting the valve 20 within a blood vein V devoid of suturing steps or any step required to completely sever the blood vein in two. Still further, the valve of this invention is believed to possess a relatively long and reliable useful life when implanted within a blood vessel. For example, a valve in accordance with the apparatus of the invention has been implanted within the jugular vein of a dog and has been found to be operable after seven months of use. Comparable valves in accordance with the present invention have been positioned with the jugular vein of seven other dogs to date and have been found to be currently operable.

It will be understood that numerous modifications and substitutions can be had to the aforedescribed embodiments without departing from the spirit of the invention.

For example, there are shown in FIGS. 8–15 alternative embodiments of the valve in accordance with the present invention having alternative leaflet means to the leaflet means 24 of the valve 20 of FIGS. 1–5. There is illustrated in FIGS. 8 and 9 a valve, generally indicated at 90, having a support ring 92 and a leaflet means 94 in the form of a circular plate 96. The support ring 22 is similar in shape to the support ring 22 of the valve 20 of FIGS. 1–5. Mounted within the support ring 92 is means defining a radially inwardly-directed flange or lip 98 defining an opening 102 and three posts 100 connected to one side of the lip 98 so as to project generally axially of the support ring 92. As best shown in FIG. 9, the posts 100 are regularly spaced about the lip 98, and the plate 98 defines three openings 106 through which the posts 100 are accepted so that the plate 96 is permitted to slide relative to and along the length of the posts 100. The plate 96 is confined upon the posts by means of the head 104 mounted at the end of the posts 100.

The valve 90 is well-suited for mounting in a blood vessel so that the flow of blood through the valve opening 102 moves in the direction of the arrow D and so that the plate 96 is positioned above the lip 98. Mounted in a blood vessel as aforesaid, the pressure differential between the upstream and downstream side of the valve 90 as a result of a heartbeat is large enough to move the plate 96 upwardly from the position illustrated in solid lines in Fig. 8, as the plate 96 is guided along the posts 100. Between heartbeats, the pressure differential between the upstream sides of the valve 90 is small enough to permit gravity to return the plate 96 from the FIG. 8 phantom condition to the FIG. 8 solid line condition as the plate 96 is guided along the posts 100. It will be understood that when the plate 96 is positioned in the FIG. 8 phantom condition, the valve 90 is open, and when the plate 96 is positioned in the FIG. 8 solid-line condition, the valve 90 is closed. Hence, the operation of the valve 90 is controlled by the differential between the blood pressure upstream and downstream of the valve 90.

With reference to FIGS. 10–12, there is shown a valve 110 having a support ring 112 leaflet means 114 in the form of a circular plate 116 comprised of magnetically-attractable material. The support ring 112 possesses the same general shape as the ring 22 of the valve 20 of FIGS. 1–5. Mounted in the ring 112 are a pair of spaced annular lips 118,120 directed radially-inwardly of the ring 112. The annular lips 118,120 define aligned openings 122,124, respectively, and as best shown in FIG. 10, opening 122 is slightly smaller in diameter than that of opening 124.

The circular metal plate 116 has a diameter which is slightly larger than that of the opening 112 so that the plate 116 is positionable, as shown in FIG. 10, across the lip 120 so as to close the opening 124. The valve 100 further includes three small compression springs 126, each of which is securely attached at one end to the lip 118 and attached at the other end to the plate 116. The springs 126 bias the plate 116 from the condition illustrated in FIG. 11, at which the plate 116 is spaced from the lip 120 and the valve 110 is open.

The valve 110 further includes three electromagnets 128 having cores which are mounted upon the lip 118. Associated with each electromagnet core is a conducting wire 130 wound thereabout. There is schematically illustrated in FIG. 13a battery 132 for energizing the electromagnets 128, but it will be understood that an alternative energy source, such as one generated from muscle contraction, can be utilized. The wire 130 is connected between the electromagnets 128 and battery 132 through a hole formed in the blood vessel for receiving the wire 130. When the electromagnets 128 are energized, the plate 116 is drawn to the magnets 128 against the force of the springs 126 so that the plate 116 overlies the lip 120 and the valve 112 is closed. When the electromagnets 128 are de-energized, the springs 126 are permitted to move the plate 116 to the FIG. 11 condition.

With reference still to FIG. 13, the electromagnets 128 and battery 132 are appropriately connected in line with a switch 134 for selectively energizing and de-energizing the electromagnets 128. Control of the operation of the valve 20 can be had by operatively associating the switch 134 with appropriate means for opening and closing the switch 134. Such means for opening and closing can be an EMG source 136 or a timer. If such means is a muscle, the myoelectric signals attending the muscle are responsible for opening and closing the switch 134.

Figure 15:
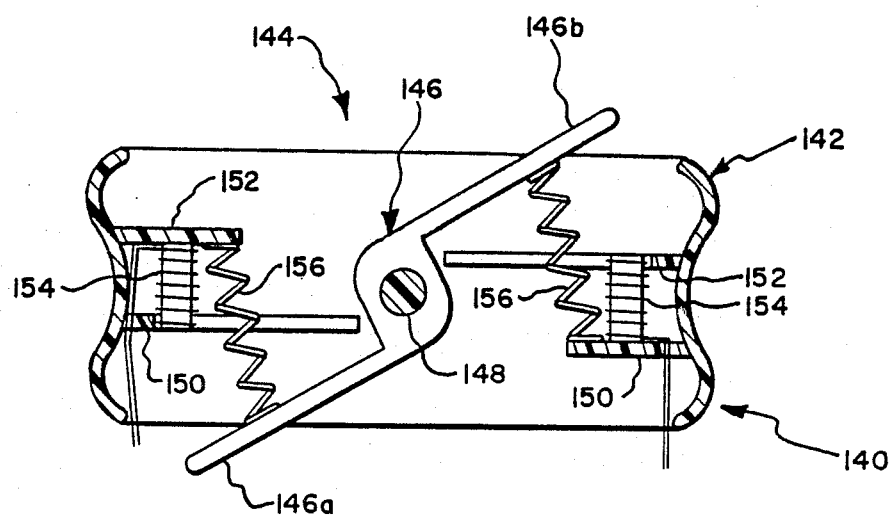
FIG. 15 is a view similar to that of FIG. 14 illustrating the FIG. 14 valve when in an open condition.
Figure 16:
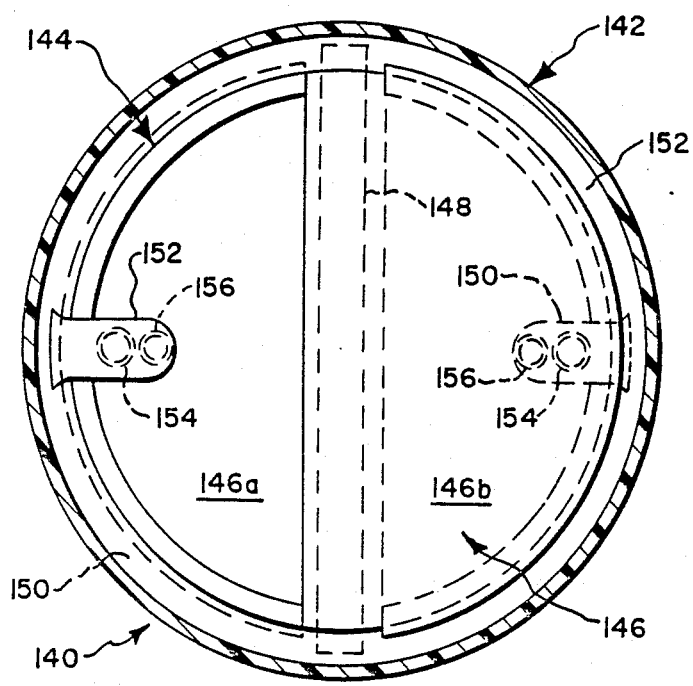
FIG. 16 is a cross-sectional view taken generally on line 16—16 FIG. 13.

With reference to FIGS. 14–16, there is shown a valve 140 having a support ring 142 and leaflet means 144 in the form of a plate 146 comprised of magnetically-attractable material and having offset flapper portions 146a and 146b. The support ring 142 possesses the same general shape as the ring 22 of the valve 10 of FIGS. 105. Mounted across the ring 142 is a shaft 148, and the plate 146 defines a transverse opening through which the shaft 148 is received permitting pivotal movement of the plate 146 between the condition shown in FIG. 14 and the condition as shown in FIG. 15. A pair of longitudinally spaced radially inwardly-directed lips 150,152 are also mounted within the ring 142 and are cooperable with the plate 146 so that when the plate 146 is positioned in the FIG. 14 condition, the valve 140 is closed and when the plate 146 is positioned in the FIG. 15 condition, the valve 140 is open.

Figure 17:
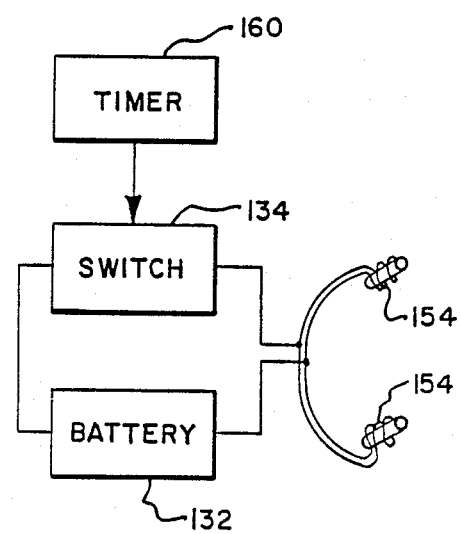
FIG. 17 is a view similar to that of FIG. 13 illustrating a control circuit for the valve of FIGS. 14-16.

The valve 140 further includes a pair of electromagnets 154,154 mounted on a corresponding lip 150,152 and arranged generally on opposite sides of the opening of the ring 142 and further includes a pair of compression springs 156,156 operatively fixed between a lip 150 and 152 of the valve 140 and a corresponding one of the plate flapper poritions 146a and 14b as best shown in FIGS. 14 and 15. Operation of the valve 140 is similar to that of the valve 110 of FIGS. 10–12 in that the energizing of electromagnets 154 pulls the plate flapper portions 146a and 146b into engagement with the lips 150,152, as shown in FIG. 14, so that the valve 140 is closed, and the de-energizing of electromagnets 154 permits the springs 156 to pivotally move the plate flapper portions 146a and 146b to the condition illustrated in FIG. 14, at which the valve 140 is open. For selectively energizing and de-energizing the electromagnets 154 and for controlling the operation of the valve 140, a system similar to the one illustrated in FIG. 13 including a battery and switch and appropriate condition between the switch and an EMG source can be utilized. Alternatively and as illustrated in FIG. 17, a similar system in which a timer or time-regulating device 160 has been substituted for the EMG of FIG. 13 source can be utilized.

Accordingly, the aforedescribed embodiments are intended for purposes of illustration and not as limitation.

I claim:

1. A method of implanting a prosthetic valve within a blood vessel comprising the steps of:
   providing a prosthetic valve including
   (a) a support ring positionable within said blood vessel and having an outer surface which includes an outwardly facing annular groove, and
   (b) leaflet means connected to said support ring in a manner permitting substantially unidirectional flow through said ring;
   forming an opening in the blood vessel at a location therealong spaced from the location at which said valve is desired to be implanted;
   inserting said prosthetic valve through the formed opening to such desired location at which said valve is to be implanted and orienting said valve so that said support ring thereof is generally in a radial plane of said blood vessel;
   providing cord means;
   tightening the cord means about the outer wall of the blood vessel such that the proximate portion of the blood vessel is caused to assume the contour of said groove: and
   holding such tigntened cord means so that said support ring is held in such desired position.

2. The method of claim 1 wherein the step of forming an opening includes the further step of cutting the blood vessel for a substantial distance around, but not all of, the circumference of said blood vessel.

3. The method of claim 2 wherein the step of cutting includes the further step of incising the blood vessel so that the incision formed therein is oriented generally within a radial plane of said blood vesel.

4. The method of claim 1 wherein the step of orienting said support ring in the radial plane of the blood vessel includes the further step of arranging the valve within the blood vessel so that the direction in which flow is permitted through the valve corresponds to the direction of flow through the blood vessel.

5. The method as defined in claim 1 wherein the step of holding is followed by the additional step of:
   closing the formed opening in the blood vessel.

6. The method of claim 5 wherein said step of closing the formed opening includes the steps of:
   positioning opposite sides of the opening adjacent one another: and
   stitching such opposite together.

7. A prosthetic valve adapted to be inserted into a blood vessel and held in a desired position therein without suturing the same, comprising:
   an annular thin-walled support ring having a substantially-constant wall thickness and having an undulating longitudinal cross-section extending between first and second annular end faces, said ring having an outer surface which includes an annular first convex surface joining said first end face, an outwardly-facing annular groove, and a second annular convex surface joining said second end face, said ring having an inner surface extending between said end faces, said inner surface having an inwardly-extending bulge to accommodate the contour of said groove; and
   leaflet means mounted on said support ring for movement toward and away from said bulge to permit only unidirectional flow through said support ring;
   whereby said valve may be inserted into said blood vessel such that the longitudinal axis of said support ring is substantially coincident with the axis of elongation of said blood vessel, and held in such position by means of a tightened cord holding a proximate portion of said blood vessel in said groove.

8. A prosthetic valve as set forth in claim 7 wherein the outer surface of said support ring is generally sinusoidal in a longitudinal direction between said end faces.

9. A prosthetic valve as set forth in claim 8 wherein the axial length of said support ring outer surface occupies a period of about 540°.

10. A prosthetic valve as set forth in claim 7 wherein said support ring outer surface is roughened.

11. A prosthetic valve as set forth in claim 7 wherein said leaflet means includes at least one leaf pivotally mounted on said support ring for movement toward and away from said bulge.

12. A prosthetic valve as set forth in claim 11 wherein said leaflet means includes two leaves pivotally mounted on said support ring for movement toward and away from said bulge.

13. A prosthetic valve as set forth in claim 11 wherein each leaf is arranged to selectively abut said bulge.

14. A prosthetic valve as set forth in claim 11, and further comprising:
   a shaft extending substantially diametrically across said ring with its end faces engaging said bulge.

15. A prosthetic valve as set forth in claim 14 wherein said shaft is press-fit into engagement with said support ring.

16. A prosthetic valve as set forth in claim 14 wherein each leaf has a barrel portion encircling said shaft.

17. A prosthetic valve as set forth in claim 7 wherein said valve means is positioned within a blood vessel, and further comprising:
   cord means adapted to be tightened about said blood vessel and valve for causing a proximate portion of said blood to assume the contour of said support ring outer surface.

* * * * *